United States Patent [19]

Leach

[11] 3,979,464

[45] Sept. 7, 1976

[54] METHYLATION OF 2,6-XYLENOL TO PRODUCE 2,3,6-TRIMETHYLPHENOL

[75] Inventor: Bruce E. Leach, Ponca City, Okla.

[73] Assignee: Continental Oil Company, Ponca City, Okla.

[22] Filed: Aug. 25, 1975

[21] Appl. No.: 607,732

[52] U.S. Cl. .................. 260/621 R; 260/624 C
[51] Int. Cl.² ............................................ C07C 39/06
[58] Field of Search ......... 260/621 R, 624 R, 624 C

[56] References Cited
UNITED STATES PATENTS

| | | | |
|---|---|---|---|
| 3,707,569 | 12/1972 | van Sorge | 260/621 R |
| 3,737,466 | 6/1973 | Sharp et al. | 260/621 R |
| 3,862,248 | 1/1975 | Jones et al. | 260/621 B |

*Primary Examiner*—James O. Thomas, Jr.
*Assistant Examiner*—W. B. Lone
*Attorney, Agent, or Firm*—Cortlan R. Schupbach, Jr.

[57] ABSTRACT

2,6-xylenol is methylated to yield 2,3,6-trimethylphenol in high selectivity in a liquid phase reaction controlled in temperature, pressure, and reactor residence time.

8 Claims, No Drawings

METHYLATION OF 2,6-XYLENOL TO PRODUCE 2,3,6-TRIMETHYLPHENOL

This invention relates to the liquid phase methylation of phenolic compounds. More specifically, this invention relates to the liquid phase methylation of 2,6-xylenol to produce 2,3,6-trimethylphenol.

2,3,6-trimethylphenol is useful as an intermediate in Vitamin E synthesis. Until direct methylation methods were developed, 2,3,6-trimethylphenol having the required purity for Vitamin E synthesis was expensive and difficult to obtain. The phenolic group in 2,6-xylenol is an orthodirector. Direct methylation techniques, therefore, tend to produce 2,4,6-trimethylphenol instead of the desired 2,3,6-trimethylphenol. Vapor phase methylations of phenols are commonly used.

Both vapor and liquid phase methylation of phenolics are well known. Examples of such methylation techniques can be found in German Pat. No. 1,817,243. Methylation of 2,6-xylenol to produce 2,3,6-trimethylphenol has been described in British Pat. No. 1,254,660. However, these known methods suffer from numerous disadvantages. When methylation is carried out in vapor phase reaction, useful catalyst life is extremely limited, and numerous undesirable by-products are formed along with the desired 2,3,6-trimethylphenol.

Liquid phase methylation allows the use of lower reaction temperatures, longer catlyst life, and fewer undesirable by-products than vapor phase reactions. However, liquid phase catalyst life, while superior to vapor phase catalyst life, it still undesirably limited. Excessively long residence time and excessively high pressures have heretofore been required. Retaining the known benefits of liquid phase methylation while overcoming the major disadvantages would therefore be of great benefit in the production of 2,3,6-trimethylphenol.

It is therefore an object of the present invention to provide an improved process for the liquid phase methylation of 2,6-xylenol. other objects will become apparent to those skilled in this art as the description proceeds.

In accordance with the present invention, an improved process for selectively increasing the yield of 2,3,6-trimethylphenol in liquid phase methylation of 2,6-xylenol is provided. The process is an improvement over the heretofore known processes in several regards and the results of this process are unexpected and dramatic. Selectivity to 2,3,6-trimethylphenol is increased nearly 50 percent over prior art methods while reaction times and pressures are reduced significantly.

Concisely, the improved process of the present invention comprises (a) reacting 2,6-xylenol with methanol in liquid phase, (b) at a temperature of from about 300°C to about 390°C, (c) at a pressure of from about 350 to about 500 pounds per square inch guage (psig), (d) at a liquid hourly space velocity (LHSV) of from about 1 to about 15, while (e) in contact with an alumina catalyst derived from aluminum alkoxide hydrolysis.

In carrying out the process, from about 0.1 to about 1.0 moles of methanol are used per mole of 2,6-xylenol, but from about 0.4 to about 0.6 moles are preferred. While prior art practices have required essentially pure 2,6-xylenol in order to carry out the methylation in liquid phase in a practical manner, the present invention can be carried out using 2,6-xylenol containing up to about 10 percent m,p substituted cresylics impurity. While pure 2,6-xylenol is of course, preferred in the present invention, very acceptable results can be obtained with relatively impure 2,6-xylenol.

The process of the present invention can be carried out efficiently in a batch reactor or a continuous flow reactor. The continuous flow reactor is preferred. In the continuous flow reactor, the residence time in the reactor is from about 10 to about 60 seconds, compared with prior art reactor times in the liquid phase of 1 hour or more.

Most preferred reaction conditions are temperatures from about 330°C to about 370°C, residence times of from 5 to 45 seconds, pressures from 375 to 450 psig, LHSV of from about 2 to about 6, and mole ratios of methanol/2,6-xylenol of from 0.3 to 0.6.

In the present invention, temperatures and pressure must be balanced to maintain a major portion of the cresylic acid component of the reactants in the liquid phase. Cresylic acid as used in this specification and claims includes all phenolic compounds. The upper limit of pressure is determined by the critical point of water. It is believed that liquid water on the catalyst reduces activity and is generally harmful to catalyst properties such as pore volume and surface area. It is critical to keep most of the water formed during the reaction in the vapor phase by the use of moderate pressure while maintaining the balance of the reactants in the liquid phase. A lower pressure limit is necessary to extend catalyst life by preventing catalyst clogging and carbonation by high molecular weight residues.

Temperature criticality is determined by conversion to the desired product. As the temperature increases, the product tends to become more heavily laden with undesirable 2,4,6-trimethyphenol instead of the more desirable 2,3,6-trimethylphenol. Higher temperatures result in higher conversion of 2,6-xylenol but lower selectivity to the desired 2,3,6-trimethylphenol, producing instead a larger percentage of 2,4,6-trimethylphenol.

Catalyst source has also been discovered to have an effect on the reaction. While the reason is not known, aluminas derived from aluminum alkoxide hydrolysis have been discovered to produce superior results obtained from other sources. Examples of such desired catalysts are CATAPAL aluminas and DISPAL aluminas sold by Continental Oil Company. These aluminas, which preferentially absorb methanol, appear to show enhanced reactivity when the cresylic acid component is in the liquid phase. In contrast, other prior art catalysts, such as titanium oxide and magnesium oxide, preferentially absorb cresylic acid and show decreased activity in the liquid phase reaction.

Selectivities to 2,3,6-trimethylphenol of up to about 70 percent can be obtained when the conversion of pure 2,6-xylenol is limited to about 25 percent. When 90 percent pure 2,6-xylenol is used, about 50 to 60 percent pure selectivity to 2,3,6-trimethylphenol is obtained with a 25 percent total conversion rate. Selectivity is defined as the total production of the desired product (also called productivity) and is obtained by multiplying the total conversion of feedstock times the percent of desired product in total phenolics converted. Uncoverted 2,6-xylenol can be recycled as a feedstock along with by-products as shown in Example 5.

The invention is more concretely described with reference to the examples below wherein all parts and percentages are by weight unless otherwise specified. The examples illustrate the invention and do not limit it.

The data disclosed herein were generated using a ½-inch stainless steel reactor containing 1/16 -inch diameter alumina extrudate. Flow in the reactor could be varied, either upward or by gravity. The reactor contained approximately 15 cubic centimeters of catalyst. The reactor was heated using an electric furnace. Temperature was measured in the center of the reactor by a thermocouple. No cooling was provided. Temperatures given in the examples are the maximum temperature of the reaction stream in the catalyst zone. After leaving the reactor, the product stream was condensed, and product distribution was determined using gas liquid chromatography (GLC). Actual percentages were measured using a computerized program which measured the area under the GLC curves.

EXAMPLE 1

CATAPAL SB alumina was used to react a 100 percent 2,6-xylenol stream at varying pressures from 400 to 700 psig. During a 1-hour sample period the temperature used was 355°C, utilizing an LHSV of 4.7. The mole ratio of methanol to phenolics was 0.60. Results are given in Table I.

TABLE I

| PRESSURE EFFECTS | | | | | | | |
|---|---|---|---|---|---|---|---|
| | Pressure psig | | | | | | |
| | 400 | 425 | 450 | 500 | 550 | 600 | 700 |
| 2,6-Dimethylanisole | 1.22 | 2.02 | 1.94 | 3.14 | 3.87 | 4.95 | 6.16 |
| 2,6-Xylenol | 64.55 | 64.59 | 67.95 | 70.68 | 70.99 | 71.04 | 73.82 |
| 2,4/2,5-Xylenol | .13 | .06 | .00 | .0 | .05 | .00 | .00 |
| 2,3-Xylenol | .16 | .21 | .00 | .04 | .43 | .03 | .03 |
| 2,4,6-Trimethylphenol | 4.24 | 3.70 | 2.57 | 1.89 | 1.56 | 1.77 | 1.63 |
| 2,3,6-Trimethylphenol | 16.30 | 16.58 | 16.19 | 14.85 | 14.45 | 14.02 | 12.40 |
| 2,3,5/2,4,5-Trimethylphenol | .13 | .06 | .14 | .18 | .22 | .22 | .17 |
| 2,3,4/3,4,5-Trimethylphenol | .79 | .87 | .56 | .40 | .33 | .22 | .17 |
| 2,3,4,6/2,3,5,6-Tetramethylphenol | 7.34 | 6.86 | 6.16 | 5.01 | 4.65 | 4.50 | 3.38 |
| 2,3,4,5-Tetramethylphenol | .41 | .47 | .15 | .25 | .22 | .21 | .29 |
| Pentamethylphenol | 4.72 | 4.58 | 4.33 | 3.56 | 3.22 | 3.04 | 1.96 |
| Product Distribution, wt % | | | | | | | |
| Methanol | 1.37 | 1.71 | 2.07 | 4.10 | 4.56 | 5.25 | 6.85 |
| Water | 6.88 | 6.69 | 6.49 | 5.34 | 5.08 | 4.70 | 3.80 |
| Total Phenolics | 91.75 | 91.60 | 91.45 | 90.55 | 90.35 | 90.05 | 89.36 |
| 2,3,6-Trimethylphenol ×Total Phenolics (Productivity) | 14.96 | 15.19 | 14.81 | 13.45 | 13.06 | 12.63 | 11.08 |

The data shown in Table I illustrates that as pressure is increased over 450 psig, the total 2,6-xylenol conversion decreases along with selectivity to the desired 2,3,6-trimethylphenol. The productivity shown at the bottom of Table I is the amount of 2,3,6-trimethylphenol in the products times the precentage of total products formed.

EXAMPLE 2

The reactor used to obtain the data in Example 2 was the same as that described for Example 1. The starting material contained 1.13 weight percent orthocresol, 10.82 percent m,p-cresol, and 88.05 weight percent of 2,6-xylenol. The mole ratio of methanol to phenolics was 0.5. A temperature of 358°C and a liquid hourly space velocity of 3.0 was used. The reaction was carried out continuously for 240 hours. No loss of activity or catalyst fouling was found. The results are shown in Table II. Composition of the feedstock is shown in the column headed by 0 hours.

TABLE II

| CATALYST LIFE IN LIQUID PHASE METHYLATION OF IMPURE 2,6-XYLENOL | | | | |
|---|---|---|---|---|
| | CUMULATIVE RUN TIME, HOURS | | | |
| | 0 | 72 | 175 | 240 |
| Mole Ratio, MeOH/Phenolics | 0.5 | | | |
| MeOH Conversion | | 93.6 | 94.3 | 94.0 |
| Product Distribution, wt % | | | | |
| Dimethyl Ether | | 0.81 | 0.81 | 0.81 |
| Methanol | 11.75 | 0.75 | 0.67 | 0.71 |
| Water | | 5.85 | 5.86 | 5.86 |
| Product | | 92.57 | 92.65 | 92.61 |
| Coke | | 0.01 | 0.01 | 0.01 |
| Product Composition, wt % | | | | |
| Anisole | 0.00 | 0.09 | 0.13 | 0.11 |
| o-Methylanisole | 0.00 | 0.43 | 0.52 | 0.48 |
| o-Cresol | 1.13 | 1.31 | 1.40 | 1.35 |
| m,p-Cresol | 10.82 | 1.71 | 1.83 | 1.77 |
| 2,6-Dimethylanisole | 0.00 | 1.71 | 1.83 | 1.77 |
| 2,6-Xylenol | 88.05 | 67.94 | 68.68 | 68.31 |
| 2,4/2,5-Xylenol | 0.00 | 2.60 | 2.64 | 2.62 |
| 2,3-Xylenol | 0.00 | 0.36 | 0.35 | 0.35 |
| 2,4,6-Trimethylphenol | 0.00 | 3.40 | 3.34 | 3.37 |
| 2,3,6-Trimethylphenol | 0.00 | 11.49 | 11.33 | 11.41 |
| 2,3,5/2,4,5-Trimethylphenol | 0.00 | 0.17 | 0.17 | 0.17 |
| Pentamethylbenzene | -0.00 | 0.50 | 0.42 | 0.46 |
| 2,3,4,6/2,3,5,6-Tetramethylphenol | 0.00 | 3.92 | 3.80 | 3.86 |

TABLE II-continued

CATALYST LIFE IN LIQUID PHASE METHYLATION OF IMPURE 2,6-XYLENOL

| | CUMULATIVE RUN TIME, HOURS | | | |
|---|---|---|---|---|
| | 0 | 72 | 175 | 240 |
| 2,3,4,5-Tetramethylphenol | 0.00 | 0.05 | 0.05 | 0.05 |
| Hexamethylbenzene | 0.00 | 0.03 | 0.03 | 0.03 |
| Pentamethylphenol | 0.00 | 2.15 | 2.00 | 2.07 |
| High Boilers | 0.00 | 2.16 | 1.49 | 1.82 |

The results of Table II show that consistent results can be obtained at long reaction times using the process of the present invention

EXAMPLE 3

A feedstock containing 11.64 percent methanol, 1.10 percent orthocresol, 7.17 percent m,p-cresol, and 80.09 percent 2,6-xylenol was put through the previously described reactor at a LHSV of 3.0 at 340°C. 400 psig back pressure was maintained. Carbon residue on the catalyst after 73 hours of continuous operation at 400 psig in the liquid phase was 2.5 percent. A vapor phase reaction was carried out. After 46 hours, the carbon residue was 18.1 percent. No change in products was observed over the 73-hour run in liquid phase, but deactivation was apparent in the vapor phase run.

EXAMPLE 4

A solution containing 0.5 mole methanol per mole of 2,6-xylenol was passed at a LHSV of 5.0 over CATAPAL SB alumina extrudate under 400 psig pressure. Reactor flow was downward. Temperature was measured at the reactor wall by a thermocouple. Temperatures were varied, and the results are shown in Table III.

The data of Table III illustrates the criticality of temperature on the ratio of 2,3,6-trimethylphenol to 2,4,6-trimethylphenol when constant pressure is maintained.

A comparison of liquid and vapor phase 2,6-xylenol methylation is set forth in tabular form in Table IV. The advantages of liquid phase methylation are apparent.

Surprisingly significant differences were found in the type of alumina catalysts used. Aluminas derived from aluminum alkoxide hydrolysis were found to be most effective. Comparative tests were carried out using CATAPAL SB aluminas from Continental Oil Company and HA1404 and HA1706 aluminas (produced by Harshaw Chemical Company). The tests were carried out in the same reaction system described above at temperatures of 358°C, LHSV of about 5.0, and 100 percent 2,6,-xylenol as a feedstock. The results are shown in Table V.

It can be seen that CATAPAL type aluminas give up to 50 percent higher selectivity to 2,3,6-trimethylphenol than other aluminas.

EXAMPLE 5

Three parts of a recycle stream similar to that generated by the reaction described in Example 4 were combined with one part of fresh feedstock to provide the feed for the instant example. A reaction was then carried out in the manner previously described for 1 hour at 355°C, 400 psig pressure, 6.3 LHSV, and 0.5 mole ratio. Composition of the reactants and products is shown in Table VI. The results show no significant loss due to use of recycle streams as a feedstock.

EXAMPLE 6

Effect of varying mole ratios and space velocities was determined in the same manner as described above. Temperature used was 355°C with a pressure of 400 psig. Results are shown in Table VII.

It will be apparent that the improved process provided herein is much superior to those provided by the prior art. Catalyst life is extended, selectivities are increased, and impure feedstocks can be used while using reaction conditions of reduced pressure and lower temperature than those taught to be necessary by the prior art.

TABLE III

LIQUID PHASE METHYLATION OF PURE 2,6-XYLENOL EFFECT OF INCREASING REACTION TEMPERATURE

| Product Distribution | 345°C | 350°C | 355°C | 360°C | 378°C |
|---|---|---|---|---|---|
| Methanol-Dimethyl Ether, Wt % | 3.5 | 3.2 | 2.6 | 1.4 | 0.6 |
| Product Composition, Wt % | | | | | |
| o-Methylanisole | 0.94 | 0.03 | 0.02 | 0.00 | 0.02 |
| m,p-Cresol | 0.00 | 0.00 | 0.00 | 0.00 | 0.77 |
| 2,6-Dimethylanisole | 4.13 | 4.28 | 3.49 | 2.18 | 0.44 |
| 2,6-Xylenol | 76.92 | 77.37 | 75.90 | 71.02 | 66.35 |
| 2,4/2,5-Xylenol | 0.00 | 0.00 | 0.00 | 0.00 | 0.56 |
| 2,3/3,5-Xylenol | 0.43 | 0.46 | 0.37 | 0.13 | 0.29 |
| 2,4,6-Trimethylphenol | 0.71 | 0.71 | 0.91 | 2.00 | 6.53 |
| 2,3,6-Trimethylphenol | 12.22 | 12.33 | 13.29 | 15.55 | 14.05 |
| 2,3,5/2,4,5-Trimethylphenol | 0.06 | 0.06 | 0.12 | 0.43 | 0.38 |
| 2,3,4/3,4,5-Trimethylphenol | 0.09 | 0.11 | 0.11 | 0.14 | 0.39 |
| 2,3,4,6/2,3,5,6-Tetramethylphenol | 2.94 | 3.05 | 3.60 | 5.17 | 6.45 |
| 2,3,4,5-Tetramethylphenol | 0.00 | 0.00 | 0.00 | 0.00 | 0.21 |
| Hexamethylbenzene | 0.05 | 0.06 | 0.10 | 0.30 | 0.34 |
| Pentamethylphenol | 1.51 | 1.53 | 2.07 | 3.07 | 2.88 |
| High Boilers | 0.00 | Tr | Tr | Tr | 0.35 |
| 2,3,6/2,4,6 Ratio | 17.2 | 17.4 | 14.6 | 7.8 | 2.2 |

TABLE IV

COMPARISON OF LIQUID AND VAPOR PHASE 2,6-XYLENOL METHYLATION

|  | 0–4 HOURS | | 4–8 HOURS | | 46 HOURS | |
|---|---|---|---|---|---|---|
|  | Liquid Phase | Vapor Phase | Liquid Phase | Vapor Phase | Liquid Phase | Vapor Phase |
| Anisole-MeOH | 1.3 | 0.7 | 1.1 | 0.5 | 0.9 | 1.6 |
| o-Me Anisole |  |  |  |  |  | 0.1 |
| o-Cresol | 1.2 | 5.0 | 1.3 | 3.6 | 1.1 | 1.5 |
| m,p-Cresol | 3.7 | 0.9 | 3.7 | 0.7 | 2.9 | 1.5 |
| 2,6-Dimethylanisole |  |  |  |  |  |  |
| 2,6-Xylenol | 67.9 | 55.8 | 68.4 | 63.3 | 68.4 | 72.7 |
| 2,4/2,5-Xylenol | 2.2 | 5.3 | 2.2 | 3.4 | 2.4 | 2.7 |
| 2,3/3,5-Xylenol | 0.3 | 1.2 | 0.3 | 0.5 | 0.4 | 0.3 |
| 2,4,6-Trimethylphenol | 3.0 | 8.0 | 2.9 | 7.2 | 3.8 | 3.8 |
| 2,3,6-Trimethylphenol | 12.2 | 9.1 | 12.3 | 9.2 | 12.7 | 8.3 |
| 2,3,5/2,4,5-Trimethylphenol | 0.6 | 3.5 | 0.4 | 1.9 | 0.2 | 0.5 |
| Pentamethylbenzene | 0.6 | 0.6 | 0.6 | 0.4 | 0.5 | 0.1 |
| 3,4,5/2,3,4-Trimethylphenol | 0.4 | 0.3 | 0.3 | 0.2 | — | — |
| 2,3,5,6/2,3,4,6-Tetramethylphenol | 3.8 | 6.0 | 3.8 | 4.8 | 4.2 | 3.3 |
| 2,3,4,5-Tetramethylphenol | 0.1 | 1.1 | 0.1 | 1.0 | 0.1 | 0.3 |
| Hexamethylbenzene | tr | 0.2 | 0.1 | 0.2 | tr | 0.1 |
| Pentamethylphenol | 1.7 | 1.9 | 1.8 | 2.8 | 2.0 | 3.1 |

TABLE V

COMPARISON OF ALUMINA CATALYSTS

|  | CATAPAL | HA1404 | HA1706 |
|---|---|---|---|
| o-Methylanisole | 0.00 | .01 | .02 |
| 2,6-Dimethylanisole | 2.79 | 4.72 | 3.85 |
| 2,6-Xylenol | 71.82 | 82.78 | 83.85 |
| 2,4/2,5-Xylenol | .11 | .08 | .06 |
| 3,5-Xylenol | .07 | 0.00 | 0.00 |
| 2,4,6-Trimethylphenol | 1.82 | 1.61 | 1.53 |
| 2,3,6-Trimethylphenol | 14.23 | 7.80 | 7.88 |
| 2,3,5/2,4,5-Trimethylphenol | .25 | .09 | .07 |
| Pentamethylbenzene | .09 | 0.00 | 0.00 |
| 2,3,4,6/2,3,5,6-Tetramethylphenol | 4.39 | 1.79 | 1.75 |
| 2,3,4,5-Tetramethylphenol | .13 | .15 | .10 |
| Hexamethylbenzene | .16 | 0.00 | 0.00 |
| Pentamethylphenol | 2.54 | .78 | .76 |
| High Boilers | 1.60 | 0.00 | 0.00 |
| 2,3,4/3,4,5-Trimethylphenol | 0.00 | 0.20 | .15 |
| Total Phenolics | 91.34 | 87.99 | 89.58 |
| Productivity | 13.00 | 6.86 | 7.06 |

TABLE VI

LIQUID PHASE METHYLATION OF 3:1 RATIO RECYCLE STREAM/FRESH FEED

| Product Distribution, Wt % | Feed | Product |
|---|---|---|
| Dimethyl Ether | 0.0 | .45 |
| Methanol | 11.15 | .29 |
| Water | 0.0 | 5.92 |
| Phenolics | 88.85 | 93.33 |

| Product Composition, Wt % | | |
|---|---|---|
| o-Methylanisole | .48 | .08 |
| o-Cresol | 0.0 | .12 |
| m,p-Cresol | 1.06 | .54 |
| 2,6-Dimethylanisole | 5.03 | 1.18 |
| 2,6-Xylenol | 92.00 | 70.60 |
| 2,4/2,5-Xylenol | .60 | 1.42 |
| 2,3-Xylenol | 0.0 | .21 |
| 2,4,6-Trimethylphenol | .46 | 2.30 |
| 2,3,6-Trimethylphenol | 0.37 | 14.45 |
| 2,3,5/2,4,5-Trimethylphenol | 0.0 | .10 |
| 2,3,4/3,4,5-Trimethylphenol | 0.0 | .30 |
| Pentamethylbenzene | 0.0 | .01 |
| 2,3,4,6/2,3,5,6-Tetramethylphenol | 0.0 | 4.28 |
| 2,3,4,5-Tetramethylphenol | 0.0 | .01 |
| Hexamethylbenzene | 0.0 | .01 |
| Pentamethylphenol | 0.0 | 2.66 |
| High Boilers | 0.0 | 1.73 |

TABLE VII

MOLE RATIO AND SPACE VELOCITY EFFECTS

| Mole Ratio | .30 | | .42 | | .55 | |
|---|---|---|---|---|---|---|
| LHSV | 4.9 | | 6.2 | | 6.1 | |
| Product Distribution, Wt % | Feed | Product | Feed | Product | Feed | Product |
| Dimethyl Ether | 0.00 | .57 | 0.00 | .37 | 0.00 | 1.50 |
| Methanol | 7.41 | .45 | 10.03 | 1.34 | 12.71 | .88 |
| Water | 0.00 | 4.96 | 0.00 | 5.35 | 0.00 | 6.84 |
| Phenolics | 92.59 | 94.02 | 89.97 | 92.94 | 87.29 | 90.78 |
| Product Composition, Wt % | | | | | | |
| Anisole | 0.00 | 0.00 | 0.00 | .05 | 0.00 | .09 |
| o-Methylanisole | 0.00 | 0.00 | 0.00 | .11 | 0.00 | .33 |
| o-Cresol | 1.07 | .29 | 1.00 | .27 | 1.00 | .71 |
| m,p-Cresol | 10.63 | 1.25 | 8.99 | 1.06 | 9.00 | 1.39 |
| 2,6-Dimethylanisole | 0.00 | 1.91 | 0.00 | 1.43 | 0.00 | 1.47 |
| 2,6-Xylenol | 88.30 | 75.14 | 90.01 | 72.00 | 90.00 | 67.13 |
| 2,4/2,5-Xylenol | 0.00 | 2.10 | 0.00 | 1.99 | 0.00 | 2.30 |
| 3,5-Xylenol | 0.00 | .14 | 0.00 | .18 | 0.00 | .21 |
| 2,4,6-Trimethylphenol | 0.00 | 1.74 | 0.00 | 2.19 | 0.00 | 3.03 |
| 2,3,6-Trimethylphenol | 0.00 | 11.85 | 0.00 | 13.25 | 0.00 | 13.94 |
| 2,3,5/2,4,5-Trimethylphenol | 0.00 | .04 | 0.00 | .09 | 0.00 | .26 |
| 2,3,4/3,4,5-Trimethylphenol | 0.00 | .04 | 0.00 | .06 | 0.00 | .13 |
| Pentamethylbenzene | 0.00 | .14 | 0.00 | .19 | 0.00 | .38 |
| 2,3,4,6/2,3,5,6-Tetramethylphenol | 0.00 | 2.79 | 0.00 | 3.74 | 0.00 | 4.42 |
| 2,3,4,5-Tetramethylphenol | 0.00 | 0.00 | 0.00 | .04 | 0.00 | .06 |
| Hexamethylbenzene | 0.00 | .14 | 0.00 | .09 | 0.00 | .09 |
| Pentamethylphenol | 0.00 | 1.35 | 0.00 | 1.86 | 0.00 | 2.14 |
| High Boilers | 0.00 | 1.08 | 0.00 | 1.39 | 0.00 | 1.90 |

While certain embodiments and details have been shown for the purpose of illustrating this invention, it will be apparent to those skilled in this art that various changes and modifications may be made herein without departing from the spirit or the scope of the invention.

I claim:

1. In a process for the liquid phase methylation of 2,6-xylenol to form 2,3,6-trimethylphenol in contact with alumina catalysts, the improvement comprising:
   a. contacting 2,6-xylenol with methanol in liquid phase,
   b. at a temperature of from about 300°C to about 390°C,
   c. at a pressure at from about 350 psig to about 500 psig,
   d. at a liquid hourly space velocity of from about 1 to about 15 while in contact with an alumina catalyst derived from aluminum alkoxide hydrolysis.

2. A process as described in Claim 1 wherein the reaction is carried out in a continuous flow reactor.

3. A process described in claim 2 wherein the residence time is from 1 to about 60 seconds.

4. A process as described in claim 1 wherein the temperature is from about 330° to about 375°C.

5. A process as described in claim 1 wherein the liquid hourly space velocity is from about 2 to about 6.

6. A process as described in claim 1 wherein water is maintained substantially in the vapor phase and cresylic acid is maintained substantially in the liquid phase.

7. A process as described in claim 1 wherein the unreacted 2,6-xylenol is recovered and reused as a feedstock.

8. A process as described in Claim 1 wherein the methanol/2,6-xylenol mole ratio is from about 0.1 to about 1.0.

* * * * *